United States Patent [19]

Yamamoto

[11] 4,155,355
[45] May 22, 1979

[54] CIRCULAR SURGICAL RETRACTOR APPARATUS

[76] Inventor: Hideo Yamamoto, 9-8, Hishiya-Nishi 4-chome, Higashi-Osaka City, Prefecture of Osaka, Japan

[21] Appl. No.: 776,851

[22] Filed: Mar. 11, 1977

[30] Foreign Application Priority Data

Feb. 1, 1977 [JP] Japan ................................ 52-10389

[51] Int. Cl.² .............................................. A61B 1/00
[52] U.S. Cl. ..................................................... 128/20
[58] Field of Search ........................ 128/20, 12, 15, 17, 128/3, 345

[56] References Cited

U.S. PATENT DOCUMENTS

| | | | |
|---|---|---|---|
| 2,013,892 | 9/1935 | Lucas | 128/20 |
| 2,623,517 | 12/1952 | Barlow et al. | 128/20 |
| 2,850,008 | 9/1958 | Resch | 128/20 |
| 3,394,700 | 7/1968 | Yamamoto | 128/20 |

*Primary Examiner*—Robert W. Michell
*Assistant Examiner*—J. Kruter
*Attorney, Agent, or Firm*—Wenderoth, Lind & Ponack

[57] ABSTRACT

A circular surgical retractor apparatus which is characterized by providing a metal bar ring having continuous arc-shaped concaves on its internal and external circumferences, providing hooks at appropriate places on the lower surface of surgical clamps having a clamping head which is a hollow and curved frame of a metal bar, and engaging the hooks with the metal bar ring.

1 Claim, 5 Drawing Figures

CIRCULAR SURGICAL RETRACTOR APPARATUS

BACKGROUND OF THE INVENTION

The present invention relates to the circular surgical retractor apparatus which is a metal bar ring with continuous arc-shaped concaves on its internal and external circumferences. Hooks are provided at appropriate places on lower surface of surgical clamps having a clamping head which is a head having a hollow and curved frame of a metal bar. The hooks engage the metal bar ring.

The present invention relates to the improvement of a surgical apparatus to expand and hold an incised part of the human body so that a surgeon can expand and hold the border of an incised part in a stable state during incising the abdomen of the human body and performing surgery on the internal organs.

A ring is placed around an incised part, the head of each clamp is attached onto the border of the incised part, the hooks of the clamps engage the ring, and the incised part is expanded freely and held to its border securely so that the surgeon can work easily, quickly and steadily without hindrance.

SUMMARY OF THE INVENTION

The present invention solves the problem of large capital investment and treatment, and offers a simple apparatus for a surgical retractor.

An object of the present invention is to enable expansion and holding of any incised part of any size in every possible position or angle without creating any pressure of weight or pain for a patient. The invention will also facilitate searching for bleeding or any other abnormal symptom in abdominal cavity, and will also enable the surgeon to perform a surgical operation on the internal organs quickly and securely without assistance. Another object of the present invention is to provide a simple structure which is easy to manufacture and use.

BRIEF DESCRIPTION OF THE DRAWINGS

The above mentioned objects and advantages of the present invention will be explained further in detail in the following description, with reference to the attached drawings, wherein.

DETAILED DESCRIPTION OF THE INVENTION

Figure 1:
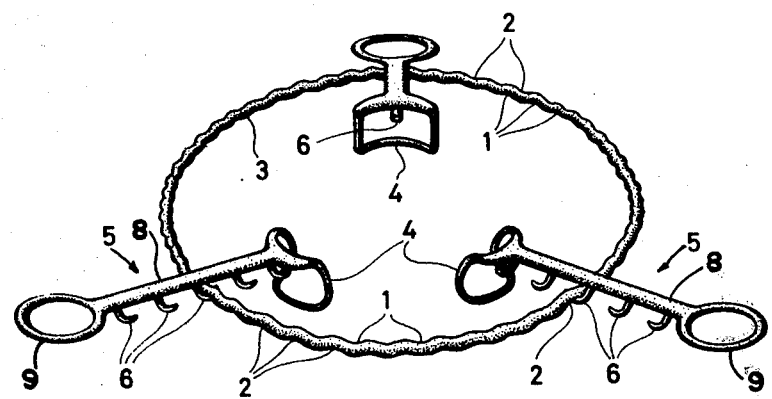
FIG. 1 is an oblique view to show a state of the clamps engaging the ring.
Figure 2:
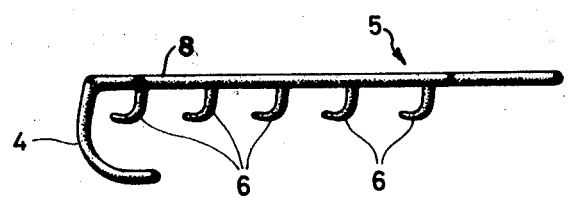
FIG. 2 is a perspective view of a surgical clamp.
Figure 3:
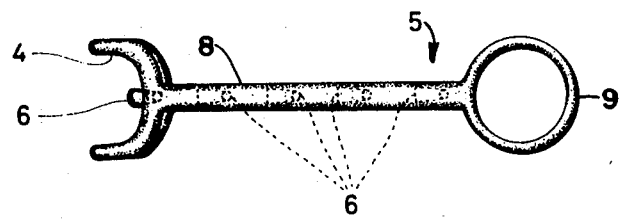
FIG. 3 is its plane view.
Figures 4, 5:
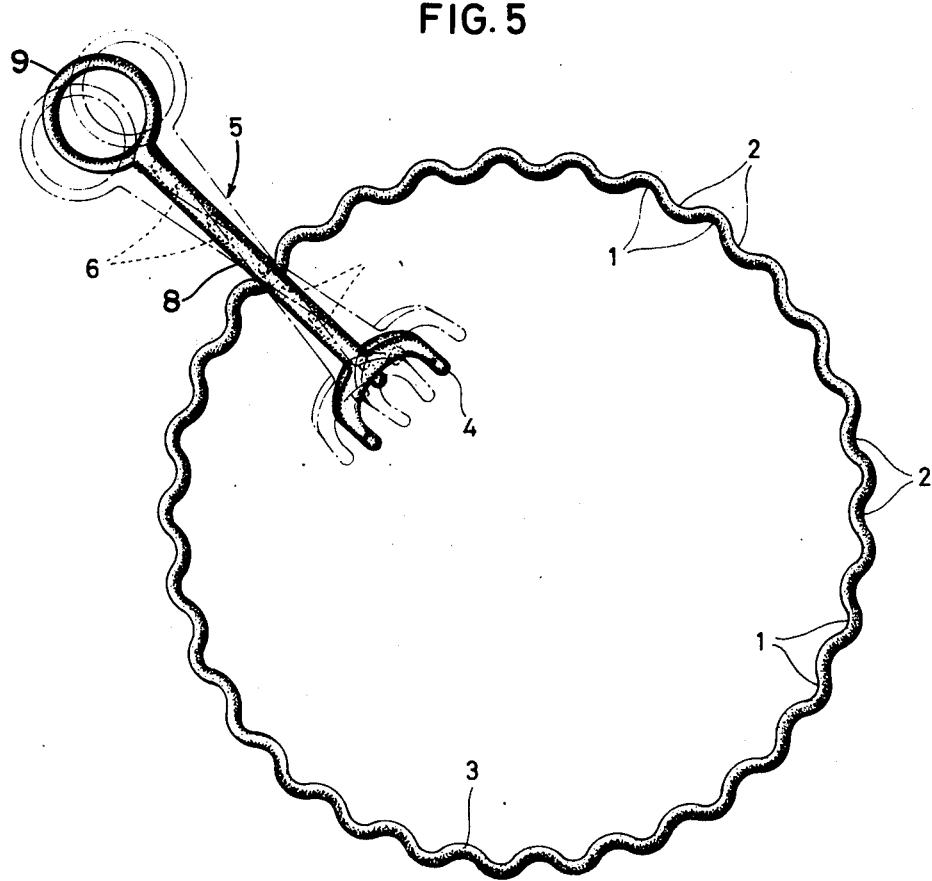
FIG. 4 is a perspective view with a partial vertical section to show a state of the clamp engaging the ring.
FIG. 5 is a plane view to show a state of the clamp engaging a specific part of the ring.

The present invention is described in detail below with reference to the drawings attached hereto.

Continuous arc-shaped concaves (1), (2) are formed on the internal and external circumference of a metal bar ring (3). Hooks (6)(6) provided at appropriate places on the lower surface of surgical clamps (5)(5) having heads (4) are hitched onto any of the arc-shaped concaves (2)(2) of the metal bar ring (3). The surgical clamps have a rod-like body portion 8 on the underside of which are located the hooks 6. The heads 4 are formed on the rod-like bodies at one end and holding rings 9 are formed at the opposite end. The above structure is quite different from a conventional apparatus which has a ring made of metal plate. That is to say, the clamps (5)(5) can swing right and left and also up and down with the point of engagement as a fulcrum. This makes it possible to keep the expanded state of the incised part smooth and flexible in every direction and position. The apparatus is so light that it gives no pressure of weight to a patient. It is possible assistants to work with fewer since the clamps engage with the ring, quickly and freely in every position, direction and angle. It also does not take long to engage or disengage the clamps and the ring.

Further, the head (4) of the clamps (5)(5) is a hollow and curved end frame on a metal bar, and is better than the conventional plate-shaped clamp head not only because it avoids damaging the organs in the abdominal cavity but also to the skin, muscles, fatty tissue, blood vessels, lymphatic glands, etc. This head 4 also allows a wide visual field for the surgeon so that he can perform his operation without over-looking any damage on a lymphatic vessel, a blood vessel and all the other organs. Moreover, the structure of the apparatus is so simple that it can be manufactured easily. It is of course possible to change the design of the apparatus within the scope of the spirit of the present invention.

What is claimed is:

1. A circular surgical retractor comprising:
   a circular metal bar ring having continuous arc-shaped concaves on its internal and external circumferences; and
   a plurality of surgical clamps engageable with said arc-shaped concaves of said ring, each surgical clamp being comprised of:
   a single rod-like body portion;
   a plurality of hooks extending downward from said body portion and engageable with said arc-shaped concaves to prevent said body portion from moving radially toward the center of said ring;
   an open, curved tissue-retaining head member at one end of said body portion; and
   a holding ring at the end of said body portion opposite said head.

* * * * *